(12) United States Patent
Das

(10) Patent No.: US 6,800,446 B2
(45) Date of Patent: Oct. 5, 2004

(54) THERAPEUTIC AND DIAGNOSTIC METHODS FOR ULCERATIVE COLITIS AND ASSOCIATED DISORDERS

(75) Inventor: Kiran M. Das, Martinsville, NJ (US)

(73) Assignee: University of Medicine & Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/779,689

(22) Filed: Feb. 8, 2001

(65) Prior Publication Data

US 2002/0013259 A1 Jan. 31, 2002

Related U.S. Application Data

(60) Provisional application No. 60/181,356, filed on Feb. 8, 2000.

(51) Int. Cl.[7] .............................................. G01N 33/53

(52) U.S. Cl. ...................................................... 435/7.1

(58) Field of Search ......................................... 435/7.1

(56) References Cited

U.S. PATENT DOCUMENTS

| 5,869,048 A | 2/1999 | Das ......................... 424/141.1 |
| 6,605,276 B1 | 8/2003 | Das | |

FOREIGN PATENT DOCUMENTS

| WO | WO 96/35449 | 11/1996 |
| WO | WO 99/48508 | 9/1999 |

OTHER PUBLICATIONS

Kesari et al. (Clin Exp Immunol 1999; 118: 219–227).*
Supplementary Partial European Search Report for Application No. EP 01 92 0971, 3 pages, dated Feb. 4, 2003.
Austin, et al., "The Majority of Epidermal T Cells in Psoriasis Vulgaris Lesions can Produce Type 1 Cytokines, Interferon–γ, Interleukin–2, and Tumor Necrosis Factor–α, Defining TC1 (Cytotoxic T Lymphocyte) and TH1 Effector Populations:[1] a Type 1 Differentiation Bias is also Measured in Circulating Blood T Cells in Psoriatic Patients," The Journal of Investigative Dermatology, vol. 113, No. 5, (Nov. 1999), pp. 752–759.
Bhagat, et al., "A Shared and Unique Peptide in the Human Colon, Eye, and Joint Detected by a Monoclonal Antibody," Gastroenterology, vol. 107, (1994), pp. 103–108.
Biancone, et al., "Autoimmunity to tropomyosin isoforms in ulcerative colitis (UC) patients and unaffected relatives," Clin Exp Immunol., vol. 113, (1998), pp. 198–205.
Biancone, et al., "Production of Immunoglobulin G and G1 Antibodies to Cytoskeletal Protein by Lamina Propria Cells in Ulcerative Colitis," Gastroenterology, vol. 109, (1995), pp. 3–12.
Brandtzaeg, "Autoimmunity and ulcerative colitis: Can two enigmas make sense together?," Gastroenterology, vol. 109, (1995), pp. 307–312.

Brion, et al., "Regulated and constitutive secretion: Differential effects of protein synthesis arrest on transport of glycosaminoglycan chains to the two secretory pathways," J. Biol. Chem., vol. 267, (Jan. 1992), Abstract only.
Coligan, "Isolation and analysis of proteins," Current Protocols in immunology, vol. 2, Ch. 8, (1994), pp. 8.0.5–8.0.7.
Coulier, et al., "Mechanism of activation of human trk oncogene," Mol. Cell Biol., vol. 9, No. 1, (Jan. 1989), pp. 15–23.
D'Argenio, et al., "Recombinant Factor XIII Replacement Therapy in Experimental Colitis in Rats," abstract, Gastroenterology: Immunology, Microbiology, and Inflammatory Disorders, vol. 112, No. 4, (Apr. 1997), p. A955.
Das, et al., "A shared and unique epitope(s) on human colon, skin, and biliary epithelium detected by a monoclonal antibody," Gastroenterology, vol. 98, (1990), pp. 464–469.
Das, et al., "Autoimmunity to Cytoskeletal Protein Tropomyosin: A Clue to the Pathogenetic Mechanism for Ulcerative Colitis," The Journal of Immunology, vol. 150, No. 6, (Mar. 15, 1993), pp. 2487–2493.
Das, et al., "Cell surface display of tropomyosin (TM), a putative autoantigen in ulcerative colitis (UC), is dependent on a colon epithelial–specific glycoprotein (CEP)," abstract, Gastroenterology: Immunology, Microbiology, and Inflammatory Disorders, vol. 112, (Apr. 1997), p. A955.
Das, et al., "The Production and Characterization of Monoclonal Antibodies to a Human Colonic Antigen Associated with Ulcerative Colitis: Cellular Localization of the Antigen by Using the Monoclonal Antibody," The Journal of Immunology, vol. 139, No. 1, (1987), pp. 77–84.
Das, et al., "Relationship of Extraintestinal Involvements in Inflammatory Bowel Disease: New Insights into Autoimmune Pathogenesis," Digestive Diseases and Sciences, vol. 44, No. 1, (1999), pp. 1–13.
Derventzi, et al., "Phorbol ester–induced reorganization the cytoskeleton in human fibroblasts during aging in vitro," Biochem. Biophys. Res. Commun., vol. 182, No. 3, (Feb. 14, 1992), pp. 1423–1428.
Dohlman, et al., "Long charge–rich alpha–helices in systemic autoantigens," Biochem. Biophys. Res. Commun., vol. 195, No. 2, (Sep. 15, 1993), pp. 686–696.
Geng, et al., "Tropomyosin Isoforms in Intestinal Mucosa: Production of Autoantibodies of Tropomyosin Isoforms in Ulcerative Colitis," Gastroenterology, vol. 114, (1998), pp. 912–922.
Gimona, et al., "Specificity of dimer formation in tropomyosins: Influence of alternatively spliced exons on homodimer and heterodimer assembly," Proc. Natl. Acad. Sci. USA, vol. 92, (Oct. 1995), pp. 9775–9780.

(List continued on next page.)

Primary Examiner—Patrick J. Nolan
(74) Attorney, Agent, or Firm—Licata & Tyrrell P.C.

(57) ABSTRACT

This invention relates to the field of therapy and diagnostic methods for ulcerative colitis. Specifically, the method comprises administering a compound or recombinant protein that inhibits interaction between CEP and human tropomyosin. Also included in the invention are methods to screen for drugs useful in treating ulcerative colitis and diagnostic methods for detecting diseases associated with an autoantigen response to hTM in affected tissue.

3 Claims, No Drawings

OTHER PUBLICATIONS

Halstensen, "Epithelial Deposition of Immunoglobulin G1 and Activated Complement (C3b and Terminal Complement Complex) in Ulcerative Colitis," Gastroenterology, vol. 98, (1990), pp. 1264–1271.

Halstensen, "Surface epithelium–related activation of complement differs in Crohn's disease and ulcerative colitis," Gut, vol. 33, (1992), Abstract only.

Hamilton, et al., "Autoimmunity in ulcerative colitis: Tropomyosin is not the major antigenic determinant of the Das monoclonal antibody, $7E_{12}H_{12}$.," Clin Exp Immunol., vol. 99, (1995), pp. 404–411.

Hassan, et al., "Expression of a unique protein on colon cancer cells that reacts with a novel monoclonal antibody and ulcerative colitis serum," Clin Exp Immunol, vol. 100, (1995), pp. 457–462.

Holmes, "Preparation of Cells and reagents for flow cytometry," Current Protocols in Immunology, Unit 5.3, (1994), pp. 5.3.1–5.3.23.

Hussain, et al., "Leprosy patients with lepromatous disease recognize cross–reactive T cell epitope in the *Mycobacterium leprae* 10–kD antigen," Clin Exp Immunol, vol. 114, (1998), pp. 204–209.

Kesari, et al., "Externalization of tropomyosin isoform 5 in colon epithelial cells," Clin Exp Immunol, vol. 118, (1999), pp. 219–227.

Kesari, et al., "Rejuvenated expression of $H–2K^b$ in RMA–S cells does not affect alloreative T cell– or natur cell–mediated lysis," Immunol. Letts, vol. 38, (1992, pp. 77–83.

Koren, et al., "Autoantibodies to the Ribosomal P Proteins React with a Plasma Membrane–related Target on Human Cells," J. Clin. Invest., vol. 89, (1992), pp. 1236–1241.

Kuchler, et al., "Membrane translocation of proteins without hydrophobic signal peptide," Curr. Opinion Cell. Biol., vol. 2, (1990), pp. 617–624.

Lees–Miller, et al., "The molecular basis for tropomyosin isoform diversity," BioEssays, vol. 13, No. 9, (Sep. 1991), pp. 429–437.

Liao, et al., "Antibody–mediated Autoimmune Myocarditis Depends on Genetically Determined Target Organ Sensitivity," J. Exp. Med., vol. 181, (Mar. 1995), pp. 1123–1131.

Lin, "Differential localization of tropomyosin isoforms in cultured non–muscle cells," J. Cell. Biol., vol. 107, (Aug. 1988), pp. 563–572.

Lin, et al., "Monoclonal antibodies against chicken tropomyosin isoforms: Production, characterization and application," Hybridoma, vol. 4, No. 3, (1985), pp. 223–242.

Lin, et al., "Topromyosin Isoforms in Nonmuscle Cells," International Review of Cytology, vol. 170, (1997), pp. 1–37.

Mayer, et al., "Evidence for function of Ia molecules on gut epithelial cells in man," J. Exp. Med., vol. 166, (Nov. 1987), pp. 1471–1483.

McCool, et al., "Regulated and unregulated pathways for MUC2 mucin secretion in human colonic LS180 adenocarcinoma cells are distinct," Biochem J., vol. 312, (1995), pp. 125–133.

Mignatti, et al., "Release of basic fibroblast growth factor, an angiogenetic factor devoid of secretory signal sequence: a trivial phenomenon or a novel secretion mechanism," J. Cell. Biochem., vol. 47, (1991), pp. 201–207.

Mion, et al., "Risk of Graft HCV Infection After Liver Transplantation for Post–Hepatitis C Cirrhosis," AASLD, (Apr. 1993), p. A955 Abstract.

Mizoguchi, et al., "Cytokine Imbalance and Autoantibody Production in T Cell Receptor–α Mutant Mice with Inflammatory Bowel Disease," J. Exp. Med., vol. 183, (Mar. 1996), pp. 847–856.

Mizoguchi, et al., "Role of Appendix in the Development of Inflammatory Bowel Disease in TCR–α Mutant Mice," J. Exp. Med., vol. 184, (Aug. 1996), pp. 707–715.

Naparstek, "The role of autoantibodies in autoimmune disease," Ann. Rev. Immunol., vol. 11, (1993), pp. 79–104.

Neu, et al., "Cardiac myosin induces myocarditis in genetically predisposed mice," J. Immunol., vol. 139, No. 11, (Nov. 1987), pp. 3630–3636.

Novy, et al., "Human fibroblast tropomyosin isoforms: Characterization of cDNA clones and analysis of tropomyosin isoform expression in human tissues and normal and transformed cells," Cell. Mot. Cytoskel., vol. 25, (1993), pp. 267–281.

Onuma, et al., "Autoimmunity in ulcerative colitis (UC): a predominant colonic mucosal B cell response against human tropomyosin isoform 5," Clin. Exp. Immnol., vol. 121 (2000), pp. 466–471.

Romagnani, et al., "T cells and cytokines in Crohn's disease," Atopic Allergy and Other Hypersensitivities, (1997), pp. 793–799.

Rubartelli, A. et al., "A novel secretory pathway for interleukin–1β, a protein lacking a signal sequence." EMBO J., vol. 9, No. 5, (1990), pp. 1503–1510.

Saitoh, et al., "Cyclosporine Inhibits Interleukin–8 Production in A Human Colon Epithelial Cell Line (HT–29)," Gastroenterology: Immunology, Microbiology, and Inflammatory Disorders, (Apr. 1996), p. A1007.

Sakamaki, "Autoantibodies against the specific epitope of human tropomyosin(s) detected by a peptide based enzyme immunoassay in sera of patients with ulcerative colitis show antibody dependent cell mediated cytotoxicity against HLA–DPw9 transfected L cells," Gut, vol. 47, (2000), pp. 236–241.

Sakamaki, et al., "Autoantibodies in sera of patients with UC recognize tropomyosin peptide associated with HLA–DPw9," abstract, Gastroenterology: Immunology, Microbiology, and Inflammatory Disorders, vol. 110, (Apr. 1996), p. A1007.

Sasiain, et al., "Interferon–gamma (IFN–γ) and tumour necrosis factor–alpha (TNF–α) are necessary in the early stages of induction of CD4 and CD8 cytotoxic T cells by *Mycobacterium leprae* heat shock protein (hsp) 65 kD," Clin Exp Immunol, vol. 114, (1998), pp. 196–203.

Sato, et al., "Secretion of the baby hamster kidney 30 kDa galactose–binding lectin from polarized and non polarized cells: A pathway independent of the endoplasmic reticulum–golgi complex," Exp. Cell. Res., vol. 207, (1993), pp. 8–18.

Warren, et al., "Forced expression of chimeric human fibroblast tropomyosin mutants affects cytokinesis," J. Cell. Biol., vol. 129, (1995), pp. 697–708.

Whitelock, "The degradation of human endothelial cell–derived perlecan and release of basic fibroblast growth factor by stromelysin, collagenase, plasmin, and heparanases," J. Biol. Chem., vol. 271, No. 17, (Apr. 26, 1996), pp. 10079–10086.

* cited by examiner

THERAPEUTIC AND DIAGNOSTIC METHODS FOR ULCERATIVE COLITIS AND ASSOCIATED DISORDERS

This application claims the benefit of priority of U.S. Provisional Application No. 60/181,356, filed on Feb. 8, 2000, the contents of which are incorporated herein by reference in its entirety.

Pursuant to 35 U.S.C. §202(c), it is acknowledged that the U.S. Government has certain rights in the invention described herein, which was made in part with funds from the National Institutes of Health, Grant No. RO1-NIADDK 47673.

FIELD OF THE INVENTION

This invention relates to the field of therapy and diagnostic methods for ulcerative colitis. Specifically, the method comprises administering a compound or recombinant protein that inhibits interaction between CEP and human tropomyosin. Also included in the invention are methods to screen for drugs useful in treating ulcerative colitis.

BACKGROUND OF THE INVENTION

Various scientific and scholarly articles are referenced throughout the specification. These articles are incorporated by reference herein to describe the state of the art to which this invention pertains.

The $Ca^{2+}$ dependence of vertebrate skeletal muscle contraction is due entirely to a set of specialized accessory proteins closely associated with actin filaments. If myosin is mixed with pure actin filaments in a test tube, myosin ATPase is activated whether or not $Ca^{2+}$ is present; in a normal myofibril, on the other hand, where the actin filaments are associated with accessory proteins, the activation of the myosin ATPase depends on $Ca^{2+}$.

One of these accessory proteins is a rigid rod-shaped molecule, called tropomyosin because of similarities to myosin in its x-ray diffraction pattern. Like the myosin tail, tropomyosin is a dimer of two identical α-helical chains which wind around each other in a coiled coil. By binding along the length of an actin filament, tropomyosin stabilizes and stiffens the filament.

Tropomyosins are present in all eukaryotic cells. Different isoforms of tropomyosin, generated through alternative splicing, are expressed in a tissue-specific manner (Less-Miller, J P, et al., Bioassays 1991; 13: 429–37). In human fibroblast tissue, at least eight isoforms of TMs have been identified. These isoforms range in molecular weights from 30–40 kDa (Lin J J-C, et al., Int Rev Cytol 1997; 170:1–38). Classically, tropomyosins are known to remain intracellular because they lack the signal sequence required for membrane insertion and translocation (Less-Miller, supra).

Human tropomyosin (hTM) is a cytoskeletal microfilament protein. A significant number of ulcerative colitis patients show a preferential immune response to hTMs, in particular, the hTM5 isoform. Thus, hTM is a candidate autoantigen in ulcerative colitis. Using lamina propria lymphocytes from mucosa of patients with ulcerative colitis and ulcerative colitis sera, an autoantibody response to hTM isoforms has been demonstrated in several independent studies, including that of Das, K M, et al. J Immunol. 1993; 150:2487–93. Such an anti-hTM autoantibody response, however, was not seen in patients with Crohn's disease. Recently, these findings were extended to an animal model of colitis using $TCR^{\alpha-/-}$ mice (Mizoguchi, A., et al. J. Exp Med. 1996; 183: 847–56). Severity of colitis in these mice is directly correlated with the increased titer of anti-TM autoantibodies and the increased number of appendicular B cells producing anti-TM autoantibodies (Mizoguchi, A., et al. J. Exp Med. 1996; 184:707–15).

In colon epithelium, the most predominantly expressed hTM isoform is hTM5 (Geng X, et al., Gastroenterology 1998; 114:912–22). It is presently unknown whether hTM5 is accessible to anti-TM autoantibodies, particularly when the target protein is expected to be exclusively intracellular. The possibility of externalization of hTM5 in colon epithelium and likelihood of the passive transport of hTM5 with a secretory protein has been considered. One likely candidate for this chaperone function is a colon epithelial-specific protein recognized by the $7E_{12}H_{12}$ monoclonal antibody.

The monoclonal antibody $7E_{12}H_{12}$ was raised using highly enriched colonic tropomyosin (earlier named as 40 kDa protein or p40) (Das K M, et al., J. Immunol 1987; 139:77–84). However, $7E_{12}H_{12}$ does not react with any of the known hTM isoforms in ELISA or immunotransblot analysis, either from muscle as well as from non-muscle epithelial cells (Das K M, et al., Gastroenterology 1997; 112:A955). However, the $7E_{12}H_{12}$ monoclonal antibody recognizes a cell membrane associated protein present exclusively in the colon epithelium (Das K M, et al. (1987) supra; Das K M, et al. (1997) supra). By immunotransblot analyses, CEP has been identified as a high molecular weight (>200 kDa) protein present in colon epithelial cells but not in small intestinal enterocytes. Among the colon cancer cell lines, LS-180, and DLD-1 cells express the $7E_{12}H_{12}$-reactive protein but HT-29 cells do not (Hassan T., et al., Clin Exp Immunol. 1995; 100:457–62).

SUMMARY OF THE INVENTION

In accordance with the present invention, it has been found that hTM5 is externalized in colon epithelium but not in small intestinal epithelium, despite the lack of a signal peptide. Furthermore, hTM5 is specifically associated with the colon epithelial-specific protein (CEP), and both are found to be secreted by LS-180 colon cancer cells.

The first aspect of the invention is due to the new appreciation that hTM is externalized in the colon epithelium and thus can stimulate the immune system and provide its antigenic role. The physical interaction of hTM with CEP is also now appreciated as important for the release of hTM outside the cell. Since an autoantibody response to hTM is associated with ulcerative colitis, the condition can be treated by decreasing the externalization of hTM in the colon. The first aspect of the invention is therefore a prophylactic and therapeutic method for treating or preventing ulcerative colitis and other diseases associated with an autoantigen response to hTM in patients in need of such a treatment. In preferred embodiments, the hTM isoform is hTM5. In a preferred embodiment, this treatment method comprises administering a compound to target cells. The compound inhibits the externalization of hTM and/or interaction between CEP and hTM within target cells. In preferred embodiments, the target cells are colon cells. In a more preferred embodiment, the compound inhibits the interaction between CEP and hTM by physically binding either within the cell. In a particularly preferred embodiment, the compound is a recombinant protein that has a functional hTM binding domain from CEP or CEP-like proteins and competes for hTM binding in vivo. In another preferred embodiment, the compound decreases or causes a decrease in the expression of the CEP protein in target cells. In another preferred embodiment, the compound reduces the release of hTM from colon cells. The compound may also prevent secretion of the CEP-hTM complex from the target cells. In a more preferred embodiment, the compound affects the organization of the cytoskeleton and/or inhibits active secretion. In a most preferred embodiment, the compound is phorbol-12-myristate-13-acetate, monensin or methylamine.

Another aspect of the invention is a prophylactic or therapeutic method to treat ulcerative colitis and other diseases associated with an autoantigen response to hTM that uses the specific binding of CEP to hTM to decrease or remove the autoantigenic nature of hTM. One embodiment of the method entails administering a recombinant protein that comprises a functional hTM binding site from CEP operably linked to a non-antigenic protein. Another embodiment of the method entails tolerization by repeated oral feeding of the hTM and/or CEP.

Another aspect of the invention is method to identify drugs that are useful for treating ulcerative colitis and other diseases associated with an autoantigen response to hTM which targets the disassociation of the CEP-hTM complex. In a preferred embodiment, intracellular association of CEP and hTM is determined by hTM secretion from human colon cells, with a decrease in hTM secretion indicative of a drug with therapeutic properties. In a more preferred embodiment, the LS-180 cells are used.

Another aspect of the invention is a diagnosis method for detecting diseases associated with an autoantigen response to hTM which entails detecting CEP-hTM complexes in affected tissue. Presence of CEP-hTM complexes are indicative of disease. In one embodiment, the complexes, or a part of them, are detected in the extracellular space of the affected tissue or by sensitized lymphocytes form colonic mucosa. In another embodiment, the CEP-hTM complexes are detected in intracellular space of the affected tissue. In a preferred embodiment, the tissue is the colon epithelium.

Other features and advantages of the present invention will be better understood by reference to the drawings, detailed description and example that follow.

DETAILED DESCRIPTION OF THE INVENTION

The specific interaction between the colon epithelium-specific protein (CEP) and the autoantigen human tropomyosin (hTM) is known to be a fundamental element in the development of the inflammatory bowel disease ulcerative colitis. Formation of CEP-hTM complexes is a requirement for the secretion of hTM from the colon epithelium and the resulting autoimmune response. Secretion of hTM in the colon epithelium and not in the small intestine is due to expression of CEP in the colon epithelium. While not limiting the functioning of the invention to any one explanation, it is likely that the intracellular interaction of the secretory protein CEP and intracellular protein hTM allows for the passive transport of hTM with CEP out of the cell.

Thus, it is likely that the externalization of hTM5 is by cotransport of hTM5 with a secretory protein. The externalization of hTM5 in the colon epithelial cells and not in small intestinal enterocytes, suggests that a colon-specific factor is involved in the process. This is supported by the fact that the $7E_{12}H_{12}$ monoclonal antibody was raised by injecting highly enriched colonic TM (previously identified as p40) (Das K M, et al. J Immunol 1987;139:77–84), and the correlation between the cell surface expression of colon-specific protein, CEP and hTM5. HTM5 is expressed intracellularly in both colonic and small intestinal epithelial cells. Yet, cell surface expression of hTM5 is seen only on colonic epithelial cells, and LS-180 cells which express CEP but not in small intestinal epithelial cells and HT-29 cells that lack CEP. This is further substantiated by the recovery of intact hTM5 and CEP in the culture medium of LS-180 cells. The coimmunoprecipitation experiments using anti-hTM5 monoclonal antibody and $7E_{12}H_{12}$ monoclonal antibody of the present invention further demonstrates physical association of hTM5 with CEP. Disappearance of 31 kDa protein, not precipitable by LC1 after immunoprecipitation with $7E_{12}H_{12}$ monoclonal antibody also suggests that CEP associated 31 kDa protein is hTM5.

CEP of the present invention is identified as a high molecular weight protein (>200 kDa). This was evidenced using colon epithelial cell and LS-180 colon cancer cell lysates as well as LS-180 culture medium by immunotransblot analysis with $7E_{12}H_{12}$. Further, the monoclonal antibody, $7E_{12}H_{12}$ did not react with any other proteins including the hTM isoforms 1–5 with molecular weights that range from 31 kDa to 40 kDa in any of the cell lysates or the culture medium that contain hTM.

CEP is a membrane associated protein that is secreted from the colon cells. hTM5 is associated with the cytoskeleton. CEP and hTM5 are believed to remain segregated in the cell. TM isoforms are involved in stabilizing actin filaments, changing cell shape, and regulating intracellular granule movement and cytokinesis (Lin J J-C, et al., (1997) supra). Actin cytoskeleton is known to be involved in the stimulus-dependent regulated exocytosis of stored secretory granules in LS-180 cells (McCool D J, et al. (1995) supra). Based on the observation that hTM5 is coimmunoprecipitated with CEP, at least a small amount of CEP may enter regulated exocytosis via stored secretory granules. This may facilitate the access of hTM5 to the secretory pathway.

The present invention demonstrates that two secretagogues, A23187 and PMA, have different effects on the secretion of CEP and hTM5. CEP secretion was unaffected in response to both A23187 and PMA. However, hTM5 secretion was increased by A23187 and inhibited by PMA. It is known that A23187 and PMA stimulate mucin secretion in LS-180 cells (McCool D J, et al. (1995) supra). However, PMA can affect the organization of cytoskeleton and thus may interfere with the secretion of hTM5 (Derventzi A., et al., Biochem Biophys Res Commun 1992; 182: 1423–28). The secretion of hTM5 may be inhibited by drugs known to inhibit Golgi-dependent and Golgi-independent secretion of proteins, such as monensin, and methylamine, respectively. Although the secretory pathway of hTM5 in LS-180 cells is not known, the inhibitory effect of these two drugs further supports the hypothesis that hTM5 is actively secreted by LS-180 cells. Cell surface expression of CEP is sensitive to monensin, suggesting the involvement of Golgi in the transport of CEP molecules. Thus, the present invention demonstrates that a $Ca^{+2}$ ionophore such as (A23187) facilitates the interaction between CEP and hTM5, whereas PMA, monensin, and methylamine interfere either with the physical interaction or cotransport of the CEP-hTM5 complex.

Cell surface expression and secretion of hTM5 are relevant to the autoimmune mechanisms in ulcerative colitis because the auto antibody response is directed to colonic tropomyosins. Colonic tropomyosins may also be available for the mucosal immune system during apoptosis of epithelial cells. A physico-chemical analysis of common structural motifs present in 109 human auto antigens has revealed that tropomyosins have the highest number of such motifs and thus, a very high propensity to act as auto antigens (Dohlman J G, et al., Biochem Biophys Res Commun 1993; 195: 686–96). The putative target antigen for autoantibodies in ulcerative colitis, such as hTM5 or hTM related peptide, may stimulate the effector immune system and can promote destruction of the epithelium by various immune mechanisms, including complement activation. Autoantibodies to the intracellular proteins are found in many autoimmune diseases and in most cases, such antibodies are considered nonpathogenic unless the target auto antigen is accessible to the antibodies. Several studies demonstrated that autoantibodies can also be internalized inside the target cells and may cause cell damage (Alarcon-Segovia D., et al., Immunol Today 1996; 17:163–64). The possibility that the intracellular target antigens are exposed to the autoantibodies is demonstrated in a mouse model for experimental autoimmune myocarditis as reported by Lio L., et al., J. Exp Med 1995; 181: 1123–31. In this model, autoantibodies to myosin cause tissue damage and inflammation, presumably via complement fixation.

The present invention indicates that CEP functions as a chaperone for the transport of hTM5. The lack of CEP in the small intestine can explain why hTM5 is not externalized by small intestinal enterocytes. This may also be relevant as to why ulcerative colitis is restricted to the colon. In the gastrointestinal tract, CEP is expressed only in colon epithelial cells. However, at extracolonic sites, CEP is expressed in skin and biliary epithelium, ciliary epithelium in eye, and also in chondrocytes. These are organs and tissues commonly involved in inflammatory bowel disease. As shown by immunoperoxidase studies using fixed formalin tissue, hTM5 is also expressed at these extraintestinal sites (Marks M, et al., Gastroenterology, 1998; 114:A1032. Thus, the present invention suggests a possible role for the CEP+hTM5 complex in the immunopathologenesis of ulcerative colitis.

The association of the CEP and hTM proteins forms the basis of the present invention relating to ulcerative colitis and associated diseases. The present invention also includes prophylactic and therapeutic methods to treat ulcerative colitis as well as associated disorders that involve disturbing the binding of CEP to hTM in order to remove the hTM autoantigen from the extracellular space. Also contemplated in the present invention are aspects that use the presence of the CEP-hTM complex in diagnostic methods for ulcerative colitis and related disorders. The present invention also includes a method to identify drugs that will be helpful for the treatment of ulcerative colitis and related diseases.

The compounds of the present invention may be any compound associated with ulcerative colitis that inhibits the externalization of hTM from colon epithelial cells. Preferably, the compound inhibits the formation of the CEP-hTM complex in a target cell. More preferably, the compound inhibits the interaction between CEP and hTM5 by physically binding to either CEP or hTM5 within the target cell. Even more preferably, the compound is a recombinant protein that acts as a functional hTM binding site from CEP. Preferably, administration of the inventive compound preferably results in a decreased expression of the CEP protein in target cells, and/or prevents secretion of the CEP-hTM complex. This inhibition of CEP-hTM complex may be achieved by affecting either the cytoskeletal organization of the cell or active secretion. Examples of suitable compounds for the above mentioned purposes are phorbol-12-myristate-13-acetate, monensin and methylamine.

The amount of compound that is administered is a therapeutically effective amount. The exact amount of compound used is a matter of preference subject to such factors as the type of condition being treated (e.g., ulcerative colitis) as well as the dosage recommended or permitted for the particular compound. In general, the amount of compound employed is the dosage required to obtain the desired result.

The present invention also extends to methods of treating or preventing ulcerative colitis and other associated diseases comprising administering a compound of the invention to a target cell. If the compound is a recombinant protein, the recombinant protein ideally comprises a functional hTM binding site found on the CEP protein. This binding site is operably linked to a non-antigenic protein.

The compounds and recombinant proteins of the present invention may be administered together with pharmaceutically acceptable carriers to provide pharmaceutical compositions which can be administered to a human orally or rectally or both, in amounts effective to provide a variety of therapeutic activity. Of course, the type of carrier will depend on the mode of administration desired for the pharmaceutical composition as is conventional in the art as well as the desired site of action. Preferably, the compound or protein is administered orally or rectally to the human.

It is especially advantageous to formulate the pharmaceutical compositions in dosage unit forms for ease of administration and uniformity of dosage. The term, "dosage unit forms" as used herein refers to physically discrete units suitable for use as a unitary dosage, each unit containing a predetermined quantity of active ingredient calculated to produce the desired therapeutic effect in association with the pharmaceutical carrier.

Extraintestinal manifestations in patients with inflammatory bowel disease are very common. The majority of these manifestations accompany the underlying disease and are influenced by its activity. Manifestations include those listed in Table 1. Because these extraintestinal manifestations are closely associated with inflammatory bowel disease, it is likely that many share their origin in the autoantigenic properties of externalized hTM. The diagnosis and treatment of these extraintestinal disorders are also contemplated with regards to the methods of the present invention.

TABLE 1

Extraintestinal manifestations of inflammatory bowel disease.

Musculoskeletal

Arthritis--colitic type, ankylosing spondylitis, isolated joint involvement
Hypertrophic osteoarthropathy--clubbing, periosteitis, metastatic
Crohn's disease
Miscellaneous--osteoporosis, aseptic necrosis, polymyositis
Skin and mouth Reactive lesions--erythema nodosum, pyoderma gangrenosum, aphthous ulcers, vesiculopustular eruption, necrotizing vasculitis
Specific lesions--fissures and fistulas, oral Crohn's disease,
drug rashes
Nutritional deficiency--acrodermatitis enteropathica (Zn), purpura (vitamin C and K), glossitis (Vitamin B), hair loss and brittle
nail (protein)
Associated diseases--vitiligo, psoriasis, amyloidosis,
epidermolysis bullosa acquisita
Hepatobiliary Specific complications--primary sclerosing cholangitis and bile duct carcinoma
Associated inflammation--autoimmune chronic active hepatitis, pericholangitis, portal fibrosis and cirrhosis,
Metabolic--fatty liver
Ocular Uveitis (iritis), episcleritis, scleromalacia, corneal ulcers, retinal vascular disease Thus, also included in the present invention are methods of screening for drugs that are useful in treating ulcerative colitis and associated diseases. One such method of screening comprises administering a candidate drug to human colon cancer cells and subsequently determining the amount of CEP-hTM complex in the cells. The amount of CEP-hTM complex is compared to either a negative control (e.g., a cell not treated with the putative drug) or to levels of CEP-hTM complex measured before administration of the putative drug. A decrease in CEP-hTM complex levels are indicative of therapeutic value of the drug. In one embodiment, this cell based assay measures, the amount of CEP-hTM complex is determined by quantifying the amount of hTM secreted from the colon cancer cells. In a highly preferred embodiment, the colon cancer cells are LS-180 cells. Detection of secreted hTM may be achieved using Western analysis immunoprecipitation as described in Example 5, below, on the serum/culture medium with an antibody specific for the secreted hTM.

Another aspect of the invention includes a cell-free assay for binding CEP-hTM complexes. The hTM and CEP proteins are combined in a cell-free system and contacted with the test compound. The cell-free system is selected from a group consisting of a cell lysate and a reconstituted protein mixture. The hTM and CEP are simultaneously expressed in a cell, and the cell is contacted with the test compound. Suitability of the test compound is determined by measuring the ability of the test compound to cause a decrease in hTM-CEP complex formation. Detection of hTM-CEP complexes may be achieved using conventional techniques including but not limited to gel electrophoresis or size exclusion gel chromatography. These methods are routine and well-known to one of ordinary skill in the art.

Also included in the present invention are expression based assays comprising a CEP gene and a promoter to form a construct, wherein the construct is operably linked to a reporter gene.

The present invention is not limited to the embodiments described and exemplified above, but is capable of variation and modification without departure from the scope of the appended claims.

Definitions

As used herein, the term, "treating" includes a therapeutic treatment of an existing or established disorder in which CEP binding to hTM is affected, or prevention of the symptoms in a subject at risk for a disorder in which CEP-hTM interaction is affected.

For purposes of the present invention, the term, "subject" is intended to include human and non-human animals. The term, "non-human animals" includes all vertebrates, e.g., mammals and non-mammals, such as non-human primates, sheep, dog, cow, chickens, amphibians, reptiles, etc. In certain embodiments, the subject is a mammal, e.g., a primate, e.g., a human.

In the present invention, the term, "administering" is intended to include routes of introducing to a subject at least one compound to perform its intended function. Administration can be carried out by any suitable route of administration, including orally, intramuscularly, or intraperitoneal.

As used herein, the term, "therapeutically effective amount" refers to the quantity of compound necessary to prevent, to cure or at least partially arrest the symptoms of the disease or disorder and its complications.

By "binding" is meant a physical association between two or more molecules which is more prolonged and/or of greater strength or affinity than would be observed following random collisions of molecules that do not bind to one another. Such binding may be transient or for a longer period.

By "screening" is meant a process in which a large number of potentially useful agents are processed in the method of this invention. It is a process distinct from a single experiment in which a single agent is studied in detail to determine its method or mode of action.

By easily detectable reporter is meant any agent or substance which can be readily detected by physical, chemical, biochemical, enzymatic or other means. Such reporters include, but are not limited to, enzymes, fluorescent, luminescent, or chromophoric molecules, antibodies labeled with any of the foregoing, and haptens and antigens that can be detected using such antibodies.

By "in vitro translation system" is meant a cell-free extract capable of translating a protein or proteins from an RNA or RNAs encoding such proteins. Such a mixture typically contains ribosomes, tRNAs, amino acids, salts, and various other factors required to sustain protein synthesis, in addition to the RNA(s) that direct protein synthesis. Such mixtures are typically prepared from sources such as, but not limited to, rabbit reticulocytes, HeLa cells, wheat germ, and *E. coli* cells; extracts prepared from such sources may be supplemented by the addition of tRNAs, amino acids, and so on, as necessary.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

The following examples are provided to describe the invention in greater detail. They are intended to illustrate, not to limit, the invention.

EXAMPLE 1

Cell Culture

Colon cancer cell lines, LS-180 and HT-29 were obtained from American Type Culture Collection, Rockville, Md. The cells were grown in Dulbecco-modified Eagle's medium (DME) supplemented with 10% fetal bovine serum, penicillin (100 U/ml), and streptomycin (100 ug/ml).

EXAMPLE 2

Monoclonal Antibodies (Monoclonal Antibodies)

Anti-TM monoclonal antibodies against five isoforms of hTM (hTM1-5) are summarized in Table 2. These monoclonal antibodies are highly isoform specific. The isotype control monoclonal antibodies, MOPC IgG and MOPC IgM, were purchased from Sigma Chemicals, St. Louis, Mo. Development and characterization of a colon epithelium-specific monoclonal antibody, $7E_{12}H_{12}$ was reported earlier (Das, K M, et al., (1987) supra). A polyclonal anti-human ribosomal protein serum, which recognizes three ribosomal proteins of molecular weights 38 kDa, 19 kDa, and 17 kDa, was purchased from Immunovision, Springdale, Ariz. Anti-actin monoclonal antibody (AC-40) was obtained from Sigma Chemicals, St. Louis, Mo.

EXAMPLE 3
Intestinal Epithelial Cells

Six surgical specimens of colon were obtained from patients with colon cancer (normal segments). Normal jejunal specimens were obtained from two patients having undergone gastric by-pass surgery for obesity. Two normal ileal specimens were obtained from two patients who underwent right hemicolectomy. Epithelial cells were prepared according to the protocol of Mayer L, et al., J. Exp Med 1987; 166:1471–83.

EXAMPLE 4
Flow Cytometry Analysis

Single cell suspensions were obtained from the cell lines by dislodging the monolayers with phosphate-buffered saline (PBS) containing 4 mM EDTA, washed twice with PBS, and viability was determined by trypan blue exclusion. Freshly prepared intestinal epithelial cells were used for flow cytometry analysis within 1 h after ensuring >90% viability. Cells were incubated with monoclonal antibodies (5 µg/ml) in PBS containing 1% bovine serum albumin, and 0.02% sodium azide and the samples were processed for analysis on a Coulter flow cytometer (Coulter Corporation, Fullerton, Calif.) as described in Holmes, K. Current Protocols in Immunology; New York: John Wiley & Sons, Inc., 1994: section 5.3.

EXAMPLE 5
Biosynthetic Labeling and Immunoprecipitation

To examine the possible association of hTM5 with the colon epithelial-specific protein (CEP), reactive with the $7E_{12}H_{12}$ monoclonal antibody, we adopted the protocols for radiolabeling, chase, and drug treatment used in the study of regulated and unregulated secretion of glycoproteins from colon cancer cells (McCool D J., et al., Biochem J. 1995; 312: 125–33; and Brion C., et al., J. Biol. Chem. 1992; 267:1477–83). LS-180 cells were labeled in methionine-free medium supplemented with 5% dialyzed fetal bovine serum with $^{35}$S-methionine (100 µCi/ml) for 16 h. Labeling was terminated by washing the cells two times with PBS followed by chase with regular DME for 2 hr. To examine the effects of stimulators and inhibitors of secretion, appropriate drugs were added during the chase period as described (McCool et al, supra; and Brion, et al., supra). Immunoprecipitations were performed on the culture medium as described in Kesari, K V and Geliebter, J. Immunol. Letts 1993: 38:77–83. After the chase, the culture medium was collected, centrifuged to remove any insoluble material, and mixed with one tenth volume of 10× lysis buffer (500 mM Tris Cl, pH 7.4 mM $MgCl_2$, 5% NP40, and protease inhibitor cocktail, Complete, Boehringer-Mannheim, GMBH, Germany). To reduce nonspecific binding, the culture medium, where LS-180 cells were grown, was preabsorbed with protein G agarose (GIBCO-BRL, NY) for 16 h at 4° C. Immunoprecipitation was carried out on ice with purified monoclonal antibodies (5 µg/ml) or ascites (10 µl/ml) for 2 h and the immune complexes were collected on Protein G Agarose. To collect IgM immune complexes, Protein G Agarose was pre-coated with affinity purified rabbit anti-mouse IgM-µ chain-specific immunoglobulins (2 mg IgG/ml gel). The immunecomplexes were washed three times by centrifugation with ice cold washing buffer-1 (50 mM Tris Cl, pH 7.4, 150 mM NaCl, 5 mM EDTA, and 0.5% NP40), followed by one wash in buffer-2 (50 mM Tris Cl, pH 7.4, 500 mM MaCl, 5 mM EDTA, and 0.5% NP40), and once with buffer-3 (50 mM Tris Cl, pH 7.4).

EXAMPLE 6
Electrophoresis

Sodium dodecyl sulfate-polyacrylamide gel electrophoresis (SDS-PAGE), and fluorography was performed as described by Coligan, J., current Protocols in Immunology. New York: John Wiley & Sons, Inc., 1994: Unit 8. Using methods well known to those of skill in the art, Western blot analysis was performed to determine the secretion of hTM5 by LS-180 cells. When LS-180 cells were subconfluent, plates were gently washed with PBS three times and the medium was replaced with serum-free DME. After 18 h incubation, culture medium was removed, centrifuged at 15,000 g for 30 min and the supernatant was concentrated by vacuum dialysis against PBS. The protein concentration was determined by Bio-Rad protein assay kit (bio-Rad Laboratories, Hercules, Calif.). The amount of proteins secreted by LS-180 cells under these experimental conditions was 1.6 ug/ml. Ten microgram protein from either LS-180 culture medium (CM) or cell lysate was analyzed in 8% or 10% SDS-PAGE followed by immunotransblot analysis using $7E_{12}H_{12}$ and anti-hTM5 monoclonal antibodies and polyclonal antibody against ribosomal proteins. The strips were then developed using chemiluminescence with peroxidase-conjugated appropriate anti-immunoglobulins (NEN Life Sciences, Boston, Mass.).

EXAMPLE 7
Experimental Results

To determine whether an isoform of tropomyosin or a tropomyosin-related molecule is expressed on the cell surface, freshly isolated colonic and small intestinal epithelial cells were examined by the flow cytometry analysis in the present invention. Colon epithelial cells were isolated from freshly obtained surgical specimens (normal segments) and were analyzed by flow cytometry using anti hTM monoclonal antibodies, CG3 (anti-hTM5), LC-24 (anti-hTM4), and CG1 (anti-hTM1) and $7E_{12}H_{12}$ (anti-CEP). The isotype control monoclonal antibody, MOPC-IgM was used for each sample to determine the background staining. Of the five monoclonal antibodies against various hTM isoforms (hTM-1-5) (see Table 2), only anti-hTM5 monoclonal antibody, CG3, showed significant staining, with a difference of two logs compared to the isotype control monoclonal antibody on the colonic epithelial cells. The colon epithelium-specific monoclonal antibody, $7E_{12}H_{12}$ used as a positive control also showed strong reactivity with the same preparation of the colon epithelial cells. (The use of monoclonal antibody $7E_{12}H_{12}$ in treating ulcerative colitis is discussed in U.S. Pat. No. 5,869,048.) However, the reactivity with the anti-hTM monoclonal antibodies against hTM isoforms 1-4 was similar to the isotype control monoclonal antibodies, MOPC-IgG or MOPC-IgM. This suggests the lack of surface expression of hTM 1-4 on colon epithelial cells. These data, in combination with other data (as discussed below), suggest the presence of hTM5 but not other hTM isoforms (hTM1-4) on the surface of colon epithelial cells.

Using CG3 monoclonal antibody in flow cytometry analysis, the inventor examined colonic epithelial cells freshly isolated from six surgically resected colon specimens. Each of the colon epithelial specimens reacted to CG3 in the flow cytometry analysis. However, there were inter-individual variations in the percent of positive cells. To minimize the artifacts, only colon epithelial cell samples with more than 90% viability were used. Using the isotype control monoclonal antibody, MOPC-IgM, although a higher background staining of colon epithelial cells was observed compared to colon cancer cells, the positive reactivity of normal colon epithelial cells by the flow cytometry analysis with CG3 monoclonal antibody was clearly evident.

To examine whether a similar CG3-reactive epitope is present on the epithelial cells from other parts of the gastrointestinal tract, freshly isolated epithelial cells from two normal ileal and two jejunal specimens were analyzed by flow cytometry. Epithelial cells isolated from ileum do not show reactivity with either CG3 or with $7E_{12}H_{12}$ monoclonal antibodies. Western blot analysis was performed using cell lysates (10 µg proteins in each lane) of three different colon and one ileal specimens with CG3 monoclonal antibody. hTM5 reactivity was clearly evident at 31 kDa. Western blot analysis was performed using $7E_{12}H_{12}$ monoclonal antibody against total cell lysates (10 µg proteins in each lane) from colon epithelial cells, jejunal epithelial cells, LS-180 colon cancer cells, and the cell free culture medium from the dish where LS-180 cells were grown after 8% SDS-PAGE. CEP was present in freshly prepared colon epithelial cells and LS-180 cells, but not injejunal epithelial cells. CEP was also seen in the LS-180 culture medium. CEP is the only protein at >200 kDa reactive to $7E_{12}H_{12}$ monoclonal antibody.

No difference was observed in the reactivity of epithelial cells from each of the four small intestinal specimens with CG3 monoclonal antibody when compared to the control MOPC-IgM. The colon epithelium-specific monoclonal antibody $7E_{12}H_{12}$, also did not show any reactivity in the small intestinal epithelial cells. The lack of surface staining of hTM5 as well as CEP with CG3 and $7E_{12}H_{12}$ monoclonal antibodies in the flow cytometry analysis on the small intestinal epithelial cells was believed to be due to the lack of expression of hTM5 and CEP in these cells. Irnmunotransblot analyses was performed using the small intestinal epithelial lysates. Colonic epithelial cell lysates were used in parallel. Both small intestinal and colonic epithelial cell extracts express hTM5 intracellularly, as evidenced by the transblot analysis probed with CG3 monoclonal antibody. However, only colon epithelial cell lysates and not small intestinal epithelial extract expressed CEP. LS-180 colon cancer cell line extract also reacted with the $7E_{12}H_{12}$ monoclonal antibody. The $7E_{12}H_{12}$ reactivity is clearly evident against a high molecular weight protein above 200 kDa. No reactivity of $7E_{12}H_{12}$ monoclonal antibody was observed with any other proteins, including the hTM isoforms (hTM1-5) expected in the range of 31 kDa to 40 kDa. Thus, the present invention demonstrates that although intracellular hTM5 is present in both colonic and small-intestinal epithelial cells, the surface expression of hTM5 is restricted to colon epithelial cells and CEP expression, both on the surface and intracellularly. Further, this surface expression of hTM5 is restricted to colon epithelial cells and is not in small intestinal enterocytes.

To establish an in vitro system, the cell surface expression of hTM5 on colon cancer cell lines LS-180 and HT-29 was examined. For colon cancer cell line studies, two anti-hTM5 monoclonal antibodies were employed. These anti-hTM5 monoclonal antibodies, CG3 and LC1, recognize two independent epitopes in the N terminal part of hTM5 encompassing amino acid residues 29–44 and 1–18, respectively (Table 2). LS-180, a colon cancer cell line, shows staining with two anti-hTM5 monoclonal antibodies, CG3, and LC-1 and with anti-CEP monoclonal antibody, $7E_{12}H_{12}$. Another colon cancer cell line, HT-29 does not show any reactivity with either anti-hTM5 or anti-CEP monoclonal antibodies. In flow cytometric analysis, LS-180 cells showed a positive signal with both CG3 and LC1. The reactivity with LC1 monoclonal antibody was stronger than CG3. However, the reactivity with CG3 monoclonal antibody was stronger in the freshly isolated colon epithelial cells. LS-180 cells also exhibit a strong signal with the colon epithelium-specific monoclonal antibody, $7E_{12}H_{12}$, used as a positive control. In the flow cytometry analysis, the colon cancer cell line HT-29 was negative for both CG3 and LC1 monoclonal antibodies as well as for the $7E_{12}H_{12}$ monoclonal antibody. Immunotransblot analysis using HT-29 cells and the anti hTM5 monoclonal antibodies and $7E_{12}H_{12}$ monoclonal antibody demonstrated intracellular presence of hTM5. However, no reactivity was observed with the $7E_{12}H_{12}$ monoclonal antibody. Thus, the reactivity patterns of HT-29 were similar to small intestinal epithelial cells.

TABLE 2

Monoclonal antibodies used in the flow cytometry and immunotransblot analyses

| Monoclonal antibody (monoclonal antibody) | Immunoglobulin (Ig) Isotype | Immunoreactive Protein | References |
|---|---|---|---|
| CG1 | IgG1 | hTM1 | 9, 17 |
| CGβ6* | IgM | hTM2 & 3 | 9, 18 |
| CG3** | IgM | hTM5 | 18 |
| LC24 | IgG1 | hTM4 | 9, 19 |
| LC1** | IgG1 | hTM5 | 19 |
| $7E_{12}H_{12}$ | IgM | CEP** | 12 |

*The monoclonal antibody Cgβ6 reacts with both hTM2 and hTM3.
**CG3 and LC1 monoclonal antibodies recognize two independent epitopes in the N terminal part of hTM5 encompassing amino acid residues 29–44 and 1–18, respectively (Alarcon-Segovia D, et al., (1996) supra).

To investigate if the surface expression on LS-180 cells is restricted to hTM5 isoform, the reactivity of LS-180 cells was examined by flow cytometry analysis using isoform specific monoclonal antibodies against four other hTM isoforms. In particular, monoclonal antibody LC24 was used for hTM4, CG1 was used for hTM1, and Cgβ6 was used for hTM2&3. The reactivity of each of these three monoclonal antibodies was similar to the isotype control antibodies, MOPC IgG or MOPC IgM.

It was found that anti-hTM4 (LC-24), anti-hTM1 (CG1), and anti-hTM 2&3 (Cgβ6), monoclonal antibodies were not reactive on the surface of LS-180 cells. Thus, the four hTM isoforms (hTM1–hTM4) were not detected on LS-180 cells. This further supports that among the five hTM isoforms, only hTM5 is expressed on the surface of LS-180 cells.

To ascertain the molecular identity of the CG3/LC1-reactive protein expressed on the surface of colonic epithelium, CG3/LC1-reactive protein was immunoprecipitated following a lactoperoxidase-radioiodination of surface proteins. This did not yield convincing reactivity most probably because of the low amount of hTM5 on the surface of the cells. Using an alternative strategy, the inventor then examined for possible release of hTM5 from the cells into the medium. Indeed, hTM5 could be recovered in the intact form from the culture medium. The presence of hTM5 was demonstrated in the cell-free culture medium and lysate of LS-180 cells using monoclonal antibodies, CG3, and LC-1 in the Western blot analysis (10 ug protein in each lane). As a positive marker, recombinant hTM5 was run in parallel. A protein of approximately 60 kDa, presumably an undissociated dimer of hTM5, was also detected by CG3. This protein is present even when highly pure recombinant hTM5 is used. Other investigators have reported hTM dimers in SDS-PAGE (Gimona M. et al., Proc Natl Acad Sci USA 1995; 92:9776–80). A Western blot analysis of cells lysate and CM with an anti-ribosome protein antibody shows the presence of two ribosomal proteins (19 and 38 kDa) in the lysate but not in culture medium. This suggests an integrity of the cells and lack of cell damage. Further, actin was examined by both immunotransblot analysis and immunoprecipitation experiment using $^{35}$S-labeled LS-180 cells with the anti-actin monoclonal antibody. The culture medium did not contain actin, further supporting the finding cell integrity and lack of cell damage.

If intracellular hTM5 is released due to cell damage or cell death, ribosomal proteins and actin could be expected in the culture medium because like hTMs, the ribosomal proteins and actin are ubiquitously and abundantly expressed intracellular proteins. The presence of hTM5 and absence of ribosomal proteins in the culture medium suggest the release of hTM5 by LS-180 cells. The LS-180 culture medium also contains $7E_{12}H_{12}$ reactive protein, CEP.

As demonstrated in the experiments described above, both hTM5 (31 kDa) and CEP (>200 kDa) are present in the LS-180 culture supernatant as shown by the immunotransblot analysis. Coimmunoprecipitation experiments were performed with LS-180culture medium using anti-hTM5 monoclonal antibody LC1 and $7E_{12}H_{12}$ monoclonal antibody. For these experiments, LS-180 cells were labeled with $^{35}$S-methionine. Culture medium was collected as described above. Immune complexes were washed as described in methods and were analyzed by 3–12% gradient SDS-PAGE-fluorography. Both CEP and hTM5 were coimmunoprecipitated by both $7E_{12}H_{12}$ and LC-1 monoclonal antibodies. The $7E_{12}H_{12}$ monoclonal antibody shows a higher amount of CEP compared to LC-1 immunoprecipitation. This suggests that there is a larger amount of CEP in the supernatant that is not bound to hTM5. When immunoprecipitated again with LC-1, the 31 kDa (hTM5) protein could not be detected. This lack of immunoprecipitation indicates complete removal of hTM5 after a single precipitation with LC1 or $7E_{12}H_{12}$ monoclonal antibodies. This observation further supports the physical association of hTM5 with CEP. Although in the immunoprecipitation experiments a few other minor proteins could be seen, the possibility of $7E_{12}H_{12}$ monoclonal antibody reacting directly with any protein other than CEP is unlikely, because Western blot analyses using lysates of both freshly isolated colon epithelial cells, LS-180 colon cancer cells as well as the LS-180 culture medium demonstrated specific reactivity only to CEP. Similarly, the specific reactivity of LC1 only to hTM5, both in the cell lysate and culture medium, is clearly evident in the immunotransblot analysis.

To investigate whether the release of hTM5 from LS-180cells is an active process, the effect of known stimulators (secretagogues), and inhibitors of secretion was examined in the present invention. Two secretatogoues, the $Ca^{+2}$ ionophore A23187, and phorbol-12-myristate-13-acetate (PMA) have been used to explore the secretory pathways in LS-180 cells (McCool D J et al (1995) supra). Culture supernatant of LS-180 cells were labeled with $^{35}$S-methionine (100 $\mu$Ci/ml) for 16 h and chased for 2 h incubated with various drugs, was immunoprecipitated and analyzed by 3–12% SDS-PAGE-fluorography. For untreated cells, 10 $\mu$l/ml of DMSO was added during the chase. Immunoprecipitation was performed using $7E_{12}H_{12}$ or LC-1 monoclonal antibodies. Controls comprised the immunoprecipitation profile of the culture supernatant from untreated cells. A 31 kDa protein was observed in the controls. The effect of secretagogues was examined by addition of 2 $\mu$M A23187 or 10 $\mu$M PMA during the chase. To examine the combined effect, A23187 (2 $\mu$M) and PMA (10 $\mu$M) were added together.

A differential effect of the two drugs on CEP and hTM5 secretion were observed. The secretion of CEP was not significantly affected by the drug treatments suggesting that a majority of CEP molecules are secreted in the absence of secretagogues. Several other proteins, including the 31 kDa protein, were coimmunoprecipitated with CEP. When the culture medium from untreated cells was immunoprecipitated with LC-1 monoclonal antibody, hTM5 (~31 kDa) and a few other proteins were seen. The CEP-associated 31 kDa protein co-migrated with hTM5, thus supporting the argument that the 31 kDa protein is hTM5. Relatively smaller amounts of protein corresponding to CEP was coimmunoprecipitated with hTM5. This is concordant with the notion that CEP and hTM5 form a complex but not all secreted CEP molecules are associated with hTM5.

A densitometric analysis of the 31 kDa band coimmunoprecipitated with CEP or hTM5 was performed with a 1 square millimeter window using a BioRad 670 densitometer after overnight exposure of the gel. These densitometric patterns of the 31 kDa protein, immunoprecipitated either by $7E_{12}H_{12}$ or LC-1 monoclonal antibodies, are similar when compared with the respective drug treatments, further suggesting that the 31 kDa protein is hTM5. Compared to only DMSO treatment, the $Ca^{+2}$ ionophore stimulated the secretion of hTM5 by 4.5 fold in the $7E_{12}H_{12}$ and by 7.8 fold in the LC-1 immunoprecipitations, whereas PMA almost totally inhibited the secretion. This was a surprising result because PMA and A23187 are known to exert a synergistic effect on the regulated secretion in LS-180 cells (McCool D J, et al., (1995) supra). When PMA and A23187 were added together, the amount of secreted hTM5 increased by 5.76 and 7.8 fold in the immunoprecipitation with $7E_{12}H_{12}$ and LC-1 monoclonal antibodies, respectively. This increase suggests the dominant effect of A23187. Furthermore, if cell lysis or death were contributing to the release of hTM5 in the culture supernatant upon treatment with a drug, one would expect to see only increased amount of hTM5 released by dead or damaged cells. Further, if cell lysis or death were responsible for hTM5 release, inhibition of hTM5 secretion would not be expected. However, inhibition of hTM5 was observed in the present invention as seen here with PMA.

The effect of two inhibitors of active secretion, namely, monensin, and methylamine, on the secretion of hTM5 was investigated. Inhibitors were added during the chase. Culture medium was immunoprecipitated with LC-1 monoclonal antibody. The rationale for the choice of these inhibitors was that monensin is known to inhibit Golgi function (McCool D J, et al., (1995) supra) whereas methylamine has been shown to inhibit extra-Golgi transport of proteins (Sato, S., et al., Exp Cell Res 1993; 207: 8–18). PMA was also included in the experiment as a known inhibitor. Secretion of hTM5 was inhibited by both monensin and methylamine.

The flow cytometric analyses of freshly isolated colon epithelial cells and a colon cancer cell line, LS-180, demonstrate the presence of hTM5 or hTM5-related molecule on the cell surface. There is some heterogeneity in the epithelial cells isolated from surgical specimens, which may be in part due to the contamination by other cell types, interindividual variations in the cell surface expression of hTM5 or due to the colon epithelial cells that do not express hTM5 on cell surface. The profile of staining of LS-180 cells with CG3, and LC1 monoclonal antibodies suggest that only a small amount of hTM5 is present on the cell surface and a portion of LS-180 cell population may not express hTM5 on the surface at a given time. It is not known whether the cell surface expression of hTM5 is cell cycle dependent or whether it is a dynamic process of transient surface expression prior to its release outside the cells. However, externalization of any amount of hTM5 is unexpected because hTMs are cytoskeletal microfilamental proteins and lack the signal peptide. Such an externalization was not seen in the small intestinal enterocytes and in HT-29 colon cancer cells studied in parallel. This is supported by several examples of the externalization of intracellular proteins lacking leader peptides and other signals for their insertion into the membranes and subsequent translocation, such as basic fibroblast growth factor (bFGF), interleukin-1, and yeast mating factor α.

The present invention is not limited to the embodiments described and exemplified above, but is capable of variation and modification within the scope of the appended claims.

What is claimed:

1. A diagnostic method for detecting inflammatory bowel disease and ulcerative colitis comprising detecting CEP-hTM5 complexes with antibodies against CEP and hTM5 in a colonic tissue wherein the presence of CEP-hTM5 is indicative of the inflammatory bowel disease and ulcerative colitis.

2. The method of claim 1 wherein the CEP-hTM5 complexes are detected in extracellular space of the tissue.

3. The method of claim 1 wherein the CEP-hTM5 complexes are detected in intracellular space of the tissue.

* * * * *